United States Patent [19]

Ueno et al.

[11] 4,436,670

[45] Mar. 13, 1984

[54] PROCESS FOR PRODUCING HYDROXYBENZONITRILES

[75] Inventors: Ryuzo Ueno, Nishinomiya; Kazuyuki Sakota, Kobe; Keiji Kawata, Sakai; Yoshiyuki Naito, Nishinomiya, all of Japan

[73] Assignee: Kabushiki Kaisha Ueno Seiyaku Oyokenkyuso, Osaka, Japan

[21] Appl. No.: 413,796

[22] Filed: Sep. 1, 1982

[30] Foreign Application Priority Data

Sep. 7, 1981 [JP] Japan .................. 56-139831

[51] Int. Cl.³ .................. C07C 120/00; C07C 121/75
[52] U.S. Cl. ................ 260/465 B; 260/465 F
[58] Field of Search ............ 260/465 B, 465 F

[56] References Cited

U.S. PATENT DOCUMENTS 3,880,905 4/1975 Norton ................ 260/465 B

FOREIGN PATENT DOCUMENTS 2332261 6/1977 France.

Primary Examiner—Dolph H. Torrence
Attorney, Agent, or Firm—Sherman & Shalloway

[57] ABSTRACT

A process for producing a hydrozybenzonitrile, which comprises reacting a hydroxybenzoic acid ester with ammonia in the vapor phase in the presence of a boron phosphate supported catalyst.

9 Claims, No Drawings

PROCESS FOR PRODUCING HYDROXYBENZONITRILES

This invention relates to a novel process for producing hydroxybenzonitriles.

For the production of hydroxybenzonitriles by vapor-phase reaction, there have been known a method which comprises reacting a lower alkyl hydroxybenzoate (with the alkyl moiety having at least 2 carbon atoms) with ammonia in the vapor phase at a reaction temperature of about 300° to about 400° C. in the presence of a catalyst composed of diatomaceous earth or pumice obtained by high temperature treatment (see Japanese Patent Publication No. 29944/1968), and a method which comprises reacting an alkyl ($C_1$-$C_4$), hydroxybenzoate with ammonia in the vapor phase in the presence of boron phosphate having a particle size of 0.2 to 0.4 mm as a catalyst (see French Patent Application No. 2332261).

According to the former method, the yield of the hydroxybenzonitrile is only 77 to 85%, and since the purity of the desired product is low, it should be separated and purified. The present inventors carefully traced the latter method, and found that the yield of the hydroxybenzonitrile is only about 80%. Furthermore, in both of these methods, the catalyst loses its activity rapidly.

It is an object of this invention to solve these problems of the known methods, and to provide an industrially advantageous process for producing hydroxybenzonitriles which are useful as intermediates for herbicides and insecticides.

The present inventors have made investigations in order to ensure sufficient contact of gases with the catalyst and to reduce the poisoning of the catalyst. As a result, they have found that the use of a supported catalyst can lead to the adjustment of the concentration of the catalyst in the vapor phase reaction system, and to the prevention of the polymerization and excessive decomposition of the starting materials or the reaction products.

Thus, according to this invention, there is provided a novel process for producing a hydroxybenzonitrile, which comprises reacting a hydroxybenzoic acid ester in the vapor phase using a boron phosphate supported catalyst.

Boron phosphate ($BPO_4$) as an active component of the supported catalyst used in this invention can be obtained by known methods such as the reaction of boric acid with phosphoric acid, the reaction of boron with diammonium hydrogen phosphate under heat, or the reaction of a boric acid ester with phosphoric acid. The mole ratio of $P_2O_5$ to $B_2O_3$ is from 0.25 to 4, preferably from 0.5 to 3. As a carrier, silica, alumina or a mixture of these can, for example, be used. Silica is especially preferred. It is preferred that the pore diameter of the carrier be distributed in the range of from 0.01 to 10 microns. The carrier is preferably in the form of pellets, granules, and spheres. It is possible to use as a promoter 0.1 to 10 mole%, preferably 0.2 to 5 mole%, of calcium carbonate, calcium sulfate, magnesium nitrate, potassium carbonate, copper nitrate, aluminum nitrate, vanadium pentoxide, selenium dioxide, manganese nitrate, cobalt nitrate, nickel nitrate, etc.

To deposit the catalyst ingredients onto the carrier, there is used, for example, a method which comprises dipping the carrier in an aqueous solution or gel-like water mixture of boron phosphate. The aqueous solution may have various concentrations from a dilute aqueous solution to a saturated aqueous solution, but an aqueous solution having a concentration of 1 to 7% by weight is preferred. Dipping is usually carried out for several minutes to about 1 hour. After dipping, the carrier is separated by filtration or centrifugal separation. Instead of the dipping, the aqueous solution of the gel-like water mixture may be sprayed, preferably in atomized formed, onto the carrier. The water adhering to the carrier is then removed by, for example, passing air under heat until the amount of the carrier becomes constant. The amount of boron phosphate on the carrier is at least about 0.5%, preferably 0.8 to 6%. After drying, the product is calcined at 150° to 800° C., preferably 300° to 700° C., for 15 minutes to several hours. Thus, a supported catalyst suitable for use in the process of this invention is obtained.

The process of this invention is performed continuously or batchwise by reacting a hydroxybenzoic acid ester with ammonia in the vapor phase by using the boron phosphate supported catalyst preferably prepared by the above process. The reaction can be carried out under atmospheric, elevated or reduced pressures. If the reaction is carried out by using alumina as an activity-maintaining agent together with the supported catalyst, or while introducing steam, the life of the catalyst increases and good results can be obtained.

Illustrative of the hydroxybenzoate are alkyl esters preferably having 1 to 10 carbon atoms, especially preferably 1 to 8 carbon atoms, of p-hydroxybenzoic acid, m-hydroxybenzoic acid or salicyclic acid. The production of p-hydroxybenzonitrile from the p-hydroxybenzoate is especially important.

The process of this invention can be practiced, for example in the following manner. The supported catalyst is filled in a reaction tube having a suitable inside diameter. The solid phase (catalyst) may be present as a fixed layer or a fluidized layer. The hydroxybenzoate is evaporated, mixed with ammonia gas, and introduced into the catalyst layer. It is also possible to dissolve the hydroxybenzoate in an inert solvent such as an aromatic hydrocarbon, and to gasify the solution. Usually, 2 to 300 moles, preferably 5 to 100 moles, of ammonia is used per mole of the hydroxybenzoate. Good results are obtained by introducing 1 to 50 moles, preferably 2 to 30 moles, per mole of the hydroxybenzoate, of steam together with ammonia. The ratio between steam and ammonia, however, is important. To minimize the formation of phenol by excessive decomposition, the mole ratio of steam to ammonia is preferably not more than 0.8, especially not more than 0.5. The reaction temperature is 200° to 600° C., preferably 300° to 500° C., and the time of contact of the reaction gas with the supported catalyst is from 0.001 second to 10 minutes, preferably 0.01 second to 2 minutes. The reaction can be carried out under a pressure of from about 50 torr to about 10 kg/cm$^2$.G. Needless to say, the excess of ammonia can be recovered and recycled in a customary manner.

According to the process of this invention, the very pure product can be obtained in a yield of at least 95%. The life of the supported catalyst is long, and for example, the reaction can be continued without activating the catalyst for a period required to obtain at least 40 parts by weight of the final product per part by weight of the supported catalyst. The catalyst having reduced activity may be activated by treating it at the same temperature as the calcining operation mentioned above while introducing air or oxygen with or without steam.

The following non-limitative Examples illustrate the present invention more specifically.

EXAMPLE 1

A reaction tube having an inside diameter of 5 cm was filled with 440 g of a supported catalyst containing 3.85% by weight of boron phosphate ($P_2O_5/B_2O_3$ mole ratio being 1) deposited on silica pellets having a pore diameter of about 0.05 micron as a carrier. Ethyl p-hydroxybenzoate and ammonia were introduced into the reaction tube at a rate of 39.5 g/hr and 323.7 g/hr respectively, and reacted in the vapor phase at 400° C. The ratio of ammonia to ethyl p-hydroxybenzoate in the gaseous mixture was 80:1, and the contact time was 10 seconds. When the reaction was continued for 19 hours, 511.1 g of p-hydroxybenzonitrile was obtained from 750.5 g of ethyl p-hydroxybenzoate. The yield was 95.0%. Gas chromatographic analysis showed that phenol was formed as a by-product in an amount of only 0.2% by weight.

EXAMPLE 2

A reaction tube having an inside diameter of 5 cm was filled with 293 g of a supported catalyst composed of boron phosphate ($P_2O_5/B_2O_3$ mole ratio=2) deposited in an amount of 2.51% by weight on the same silica carrier as used in Example 1. Ethyl p-hydroxybenzoate and ammonia were introduced into the reaction tube at a rate of 72.3 g/hr and 148 g/hr, and reacted in the vapor phase at 385° C. The mole ratio of ammonia to ethyl p-hydroxybenzoate in the gaseous mixture was 20:1, and the contact time was 10 seconds. When the reaction was continued for 8 hours, 388.9 g of p-hydroxybenzonitrile was obtained from 578.4 g of ethyl p-hydroxybenzoate. The yield was 93.8% by weight. Gas chromatographic analysis showed that the amount of by-product phenol was only 0.5% by weight.

EXAMPLE 3

A reaction tube having an inside diameter of 5 cm was filled with 350 g of a supported catalyst containing 3.85% by weight of boron phosphate ($P_2O_5/B_2O_3$ mole ratio=1) deposited on the same silica carrier as in Example 1. Ethyl p-hydroxybenzoate, ammonia and steam were introduced into the reaction tube at a rate of 38.6 g/hr, 263.2 g/hr, and 41 g/hr, respectively, and reacted in the vapor phase at 400° C. The mole ratio of ammonia, steam and ethyl p-hydroxybenzoate in the gaseous mixture was 6.6:9.8:1, and the contact time was 9.4 seconds. When the reaction was continued for 204 hours, 5.363 kg of p-hydroxybenzonitrile was obtained from 7.784 kg of ethyl p-hydroxybenzoate. The yield was 95.0% by weight. Gas chromatographic analysis showed that only 2.1% by weight of phenol was formed as a by-product. The amount of p-hydroxybenzonitrile obtained per part by weight of the supported catalyst was more than 15.3 parts by weight.

EXAMPLE 4

A reaction tube having an inside diameter of 5 cm was filled with 440 g of a supported catalyst composed of 4.35% by weight of boron phosphate ($P_2O_5/B_2O_3$ mole ratio=1) deposited on the same silica carrier as in Example 1. Ethyl p-hydroxybenzoate, ammonia and steam were introduced into the reaction tube at a rate of 71.6 g/hr, 281.9 g/hr and 43.4 g/hr, respectively, and reacted in the vapor phase at 410° C. The mole ratio of ammonia, steam and ethyl p-hydroxybenzoate in the gaseous mixture was 38.5:5.6:1, and the contact time was 7.5 seconds. When the reaction was continued for 92 hours, 4.477 kg of p-hydroxybenzonitrile was obtained from 6.587 kg of ethyl p-hydroxybenzoate. The yield of the product was 94.8% by weight. Gas-chromatographic analysis showed that only 1.2% by weight of phenol was formed as a by-product. The amount of p-hydroxybenzonitrile obtained was more than 10.1 parts by weight per part by weight of the supported catalyst.

EXAMPLE 5

A reaction tube having an inside diameter of 5 cm was filled with a thorough mixture of 195 g of alumina and 195 g of a supported catalyst composed of 3.94% by weight of boron phosphate ($P_2O_5/B_2O_3$ mole ratio=1) deposited on the same silica carrier as in Example 1. Ethyl p-hydroxybenzoate, ammonia and steam were introduced into the reaction tube at a rate of 75 g/hr, 268.8 g/hr and 40.7 g/hr, respectively, and reacted in the vapor phase at 395° C. The mole ratio of ammonia, steam and ethyl p-hydroxybenzoate was 35:5:1 in the gaseous mixture, and the contact time was 5 seconds. When the reaction was carried out for 308 hours, 15.75 kg of p-hydroxybenzonitrile was obtained from 23.1 kg of ethyl p-hydroxybenzoate. The yield was 95.1% by weight. Gas-chromatographic analysis showed that only 2.5% by weight of phenol was formed as a by-product. The amount of p-hydroxybenzonitrile obtained per part by weight of the supported catalyst was more than 40.3 parts by weight.

EXAMPLE 6

A reaction tube having an inside diameter of 5 cm was filled with 293 g of a supported catalyst composed of 3.75% by weight of boron phosphate ($P_2O_5/B_2O_3$ mole ratio=1) deposited on an alumina carrier spherical alumina carrier having a pore diameter of about 1 micron. Octyl salicylate and ammonia were introduced into the reaction tube at a rate of 108.9 g/hr and 148 g/hr, respectively, and reacted in the vapor phase at 415° C. The mole ratio of ammonia to octyl salicylate in the gaseous mixture was 20:1, and the contact time was 11 seconds. When the reaction was continued for 8 hours, 375.3 g of o-hydroxybenzonitrile was obtained from 871.2 g of octyl salicylate. The yield was 90.5% by weight. Gas-chromatographic analysis showed that only 2.6% by weight of phenol was formed as a by-product.

What we claim is:

1. A process for producing a hydroxybenzonitrile, which comprises reacting a hydroxybenzoic acid ester with ammonia in the vapor phase in the presence of a boron phosphate supported catalyst.

2. The process of claim 1 wherein boron phosphate is supported on silica or alumina as a carrier.

3. The process of claim 1 or 2 wherein the reaction is carried out in the further presence of steam.

4. The process of any one of the claims 1 or 2 wherein the hydroxybenzoic acid ester is an alkyl ester having 1 to 10 carbon atoms of hydroxybenzoic acid.

5. The process of any one of claims 1 or 2 wherein the hydroxybenzoic acid ester is an alkyl ester having 1 to 10 carbon atoms of p-hydroxybenzoic acid.

6. The process of claim 2 wherein the pore diameter of the silica carrier or alumina carrier is in the range of from 0.01 to 10 microns.

7. The process of claim 3 wherein the mole ratio of steam to ammonia is not more than 0.8.

8. The process of claim 4 wherein the reaction is carried out in the presense of steam.

9. The process of claim 5 wherein the reaction is carried out in the presence of steam.

* * * * *

UNITED STATES PATENT AND TRADEMARK OFFICE
CERTIFICATE OF CORRECTION

PATENT NO. : 4,436,670
DATED : March 13, 1984
INVENTOR(S) : RYUZO UENO, ET AL.

It is certified that error appears in the above—identified patent and that said Letters Patent is hereby corrected as shown below:

For [73] Assignee:

Delete "Kabushiki Kaisha Ueno Seiyaku Oyokenkyuso", insert --Kabushiki Kaisha Ueno Seiyaku Oyo Kenkyujo--.

Signed and Sealed this

Fourth Day of September 1984

[SEAL]

Attest:

GERALD J. MOSSINGHOFF

Attesting Officer　　　Commissioner of Patents and Trademarks